(12) United States Patent
Hermle

(10) Patent No.: US 9,386,970 B2
(45) Date of Patent: Jul. 12, 2016

(54) MEDICAL INSTRUMENT WITH SHAFT ROTATABLE RELATIVE TO HANDLE

(71) Applicant: Karl Storz GmbH & Co. KG, Tuttlingen (DE)

(72) Inventor: Rainer Hermle, Gosheim (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 79 days.

(21) Appl. No.: 14/254,471

(22) Filed: Apr. 16, 2014

(65) Prior Publication Data

US 2014/0316211 A1    Oct. 23, 2014

(30) Foreign Application Priority Data

Apr. 18, 2013    (DE) .................. 10 2013 103 905

(51) Int. Cl.
| | | |
|---|---|---|
| A61B 17/02 | (2006.01) | |
| A61B 1/313 | (2006.01) | |
| A61B 17/00 | (2006.01) | |
| A61B 1/00 | (2006.01) | |
| A61B 17/29 | (2006.01) | |

(52) U.S. Cl.
CPC .............. *A61B 17/02* (2013.01); *A61B 1/00135* (2013.01); *A61B 1/313* (2013.01); *A61B 17/00008* (2013.01); *A61B 1/00128* (2013.01); *A61B 2017/0046* (2013.01); *A61B 2017/00477* (2013.01); *A61B 2017/291* (2013.01)

(58) Field of Classification Search
CPC ................. A61B 2019/4889; A61B 17/00008; B25B 23/0028
See application file for complete search history.

(56) References Cited

U.S. PATENT DOCUMENTS

| | | | |
|---|---|---|---|
| 5,261,888 A * | 11/1993 | Semm | A61B 17/3421 604/158 |
| 5,681,262 A | 10/1997 | Isse | |
| 5,902,233 A | 5/1999 | Farley et al. | |
| 6,105,473 A * | 8/2000 | Huang | B25B 15/00 81/177.75 |
| 6,129,661 A * | 10/2000 | Iafrati | A61B 1/042 600/114 |
| 6,139,489 A | 10/2000 | Wampler et al. | |
| 6,413,208 B1 * | 7/2002 | Schollhorn | A61B 17/00008 600/131 |
| 2001/0012942 A1 | 8/2001 | Estes et al. | |
| 2003/0220547 A1 | 11/2003 | Holland et al. | |
| 2004/0040423 A1 * | 3/2004 | Hung | B25B 15/02 81/177.75 |
| 2012/0239009 A1 * | 9/2012 | Mollere | A61B 17/07207 606/1 |

FOREIGN PATENT DOCUMENTS

| | | |
|---|---|---|
| DE | 19906260 A1 | 9/1999 |
| DE | 19827360 A1 | 1/2000 |
| WO | 9952418 A1 | 10/1999 |

* cited by examiner

*Primary Examiner* — Jan Christopher Merene
(74) *Attorney, Agent, or Firm* — Whitmyer IP Group LLC

(57) ABSTRACT

A medical instrument with an elongate shaft which, at a distal end, carries a spatula, and, in a proximal end area, has a shaft head on which a laterally protruding handle is arranged. The shaft is rotatable relative to the handle about a rotation axis parallel to a longitudinal axis of the shaft.

12 Claims, 6 Drawing Sheets

MEDICAL INSTRUMENT WITH SHAFT ROTATABLE RELATIVE TO HANDLE

FIELD OF THE INVENTION

The present invention relates to a medical instrument with an elongate shaft which, at a distal end, carries a spatula, and, in a proximal area, has a shaft head on which a laterally protruding handle is arranged.

BACKGROUND OF THE INVENTION

The laid-open application DE 198 27 360 A1 discloses a medical instrument with an elongate shaft which, at the distal end, has a spatula tip, and in the proximal area of which a laterally projecting handle is arranged. The handle is connected to the shaft in such a way that an outer face of the instrument directed away from the handle has a substantially uniform surface extending continuously from the distal to the proximal end. The known instrument also has an endoscope lens system with an eyepiece inclined, substantially on the same side as the handle, in relation to a longitudinal central axis of the shaft. The known medical instrument is intended for endoscopic removal of the vena saphena magna, wherein the instrument is inserted through an incision in the knee area and is advanced along the vein as far as the inguinal region or the ankle region almost parallel to the skin surface. The endoscopic intervention with visual monitoring permits removal of the vena saphena magna in a way that is particularly gentle on tissue, and only a single, relatively short scar is left behind.

Endoscopic methods are also known in thyroid surgery. In the technique known as EndoCATS (endoscopic cephalic access thyroid surgery), an incision is made in the area of the scalp covered by hair behind the ear. A retractor spatula is advanced through natural spaces into the thyroid bed (spatium de Quervain). After the operation, the incision is covered by regrowth of hair on the head, such that the scar remains hidden from view. In order to guide the spatula through the natural spaces to the actual operating site, the spatula is rotated about the longitudinal axis of the instrument depending on the position and direction of the usable spaces during the advance movement. However, since the proximal end area of the instrument lies closely on the scalp, the handling of the instrument in order to perform such a rotation movement is made difficult and, in particular, the available angle range is relatively narrow.

SUMMARY OF THE INVENTION

It is an object of the present invention to improve the handling of a medical instrument of the type in question, in particular of a medical instrument intended for the EndoCATS technique.

A medical instrument according to the invention comprises an elongate shaft which, at a distal end, i.e. the end remote from the user, carries a spatula, and, in a proximal end area, i.e. the end area near the user, has a shaft head on which a laterally protruding handle is arranged. In particular, the spatula is flattened out or spoon-shaped and is designed to be atraumatic, as a result of which the passage through natural spaces is made easier and possible tissue damage is minimized. The shaft head can be rigidly connected to the shaft or can form an integral component part of the shaft.

The handle is designed in particular to be gripped by one hand and can be angled in order to improve handling. The shaft of the medical instrument can have a continuous channel for the insertion of an endoscope lens system, and the shaft head can have a coupling for securing the endoscope lens system in the shaft. Moreover, further continuous channels can be present, which can be used for example for rinsing and/or suctioning.

According to the invention, the shaft is rotatable relative to the handle about a rotation axis parallel to a longitudinal axis of the shaft. The rotation axis can coincide with a longitudinal central axis of the shaft or can be offset relative thereto.

By virtue of the fact that the shaft is rotatable relative to the handle about a longitudinal central axis of the shaft or an axis parallel thereto, it is possible to rotate the shaft within a larger range of angles than would be possible with a rotation of the handle alone or of a rigid instrument. This is especially advantageous when the rotation of the handle is limited by the operating conditions, as is the case in the EndoCATS technique where the proximal end area of the instrument bears on the head of the patient. The use of natural spaces for advancing the spatula to the operating site is thus made easier.

According to a preferred embodiment of the invention, the shaft is mounted so as to be rotatable relative to the handle against a frictional resistance. The frictional resistance comprises in particular a static friction, which has to be overcome to initiate a rotation movement, but it can also comprise a kinetic friction during a rotation movement. By virtue of the fact that the rotation movement of the shaft relative to the handle is braked by the frictional resistance, the handling of the medical instrument is further improved. In particular, by rotating the handle, it is possible to rotate the shaft about a longitudinal axis, or about a rotation axis parallel to the longitudinal axis of the shaft, even against a certain resistance exerted by the tissue or against torques that are exerted by supply lines possibly secured on the shaft. This too makes it easier to use natural spaces for advancing the spatula.

Advantageously, the frictional resistance is generated by a spring-mounted brake pin or by a spring-mounted pressure piece. A simple and functionally reliable arrangement is created in this way, and, through the choice of material and the choice of the spring force, it is possible to ensure a frictional resistance that is optimal for the handling.

Preferably, the brake pin or the pressure piece is assigned to the handle and acts on a friction surface assigned to the shaft head. In particular, the brake pin can be guided in a bore of the handle, which bore also accommodates a spring for generating a desired contact pressure with which the brake pin is pressed onto the friction surface. By virtue of the brake pin or the pressure piece being assigned to the handle, the installation space present in the handle can be used for this purpose and the shaft head can be made particularly compact.

According to a preferred embodiment of the invention, the shaft is flattened out on a top face directed away from the handle and, with the top face of the shaft head directed away from the handle, forms an at least largely flat surface which extends substantially continuously from the shaft head to the distal end of the shaft and which is in particular free of projections and/or steps. The flat surface can also be made slightly concave and form a shallow trough, which extends from the proximal end area of the instrument as far as the distal end of the shaft. In particular, the substantially flat surface of the shaft head and of the shaft is arranged with respect to a central position of the handle. By virtue of the fact that the shaft and the shaft head form, on the outer face of the instrument, a continuous and substantially flat surface, it is possible to insert the shaft through an incision particularly close to the body of the patient.

The spatula is preferably spoon-shaped and defines a hollow space inside the spatula. A further hollow space in the tissue, adjacent to the inner hollow space, can be held open by the spatula; insufflation of gas is not generally necessary to create the hollow space. Surgical manipulations, for example the removal of a thyroid lobe, can be performed in the hollow space with endoscopic monitoring, for which purpose an endoscope lens system is advanced through an optics channel arranged in the shaft, and endoscopic instruments are advanced along the shaft as far as the area of the spatula. The hollow space defined by the spatula is preferably open toward the outer face of the instrument directed away from the handle, such that the substantially flat surface formed by the shaft and the shaft head is arranged on the same side of the instrument as the hollow space formed by the spatula and merges into said hollow space. This makes it easier to insert and operate endoscopic instruments that are inserted along the shaft as far as the hollow space of the spatula or a hollow space held open by the spatula; this applies particularly in the case where the flat surface has a trough-shaped design or in the case where the shaft has a shallow kidney-shaped cross section.

Moreover, it is preferable that the handle is guided relative to the shaft head in at least one arc-shaped groove that extends transversely with respect to the longitudinal axis of the shaft. The central point of the arc of the at least one arc-shaped groove defines the rotation axis about which the handle can be rotated relative to the shaft. The rotation axis can, for example, be the central longitudinal axis of the optics channel through which an endoscope lens system can be pushed into the shaft, although it can also lie, for example, outside this central longitudinal axis or also outside the shaft or the shaft head. By virtue of the fact that the handle is guided relative to the shaft head in at least one arc-shaped groove, an optimal arrangement of the rotation axis relative to the longitudinal axis of the shaft is permitted.

This design of the medical instrument, in which the handle is guided relative to the shaft head in at least one arc-shaped groove that extends transversely with respect to the longitudinal axis of the shaft, is particularly advantageous if the shaft, as described above, is flattened toward an outer face directed away from the handle and forms, with the outer face of the shaft head directed away from the handle, an at least largely flat or slightly concave surface extending substantially continuously from the shaft head to the distal end of the shaft. In this case, the guiding of the shaft in the arc-shaped groove makes it possible to avoid a situation where the guiding of the handle in the direction of the work space interferes on the outer face of the shaft head directed away from the handle. In this way, the medical instrument can be guided particularly close to the body of the patient, and the insertion of endoscopic working instruments parallel to the shaft is made easier.

The arc-shaped groove preferably has an undercut, by means of which the handle is held and guided with a form fit on the shaft head. In particular, the groove can advantageously have a T-shaped or a dovetail-shaped profile. This has the particular advantage that, during the rotation movement relative to the shaft head, the handle is guided solely by the engagement in the groove, such that the entire cross section of the shaft and of the continuation of the shaft inside the shaft head can remain free of guiding and holding elements for guiding and holding the handle.

Particularly preferably, the shaft head has the arc-shaped groove, and the handle has at least one projection for form-fit engagement in the groove. In particular, the projection is likewise arc-shaped and complements the cross section of the groove. As a result, safe guiding of the handle in order to achieve the rotatability of the handle relative to the shaft is permitted in a particularly simple way.

Preferably, the angle range of the rotation between handle and shaft is limited by at least one abutment pin, preferably two abutment pins, for example to an angle range of ±35° with respect to a central position. It is also preferable for the one or more abutment pins to be arranged on the shaft head. In this way, the handling of the instrument is further improved. In particular, the arrangement of the one or more abutment pins on the shaft head allows the user to rotate the shaft head, and therefore the shaft, relative to the handle by gripping the one or more abutment pins.

Advantageously, the handle can be connected releasably to the shaft head. For this purpose, provision can be made, for example, that at least one abutment element, in particular one abutment pin, is releasably connected to the shaft head, and that, after removal of the at least one abutment pin, the handle in the groove can be moved beyond the range limited by the abutment pin and in this way can be separated from the shaft head. By virtue of the fact that the handle can be released from the shaft head, cleaning and sterilization of the instrument are made easier.

Preferably, the connection between the handle and the shaft head is not free of play. In this way, the assembly and disassembly of the handle, and the handling of the instrument, are made easier.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

Further aspects of the invention will become clear from the following description of a preferred illustrative embodiment and from the attached drawing, in which.

DETAILED DESCRIPTION OF THE INVENTION

Figure 1:
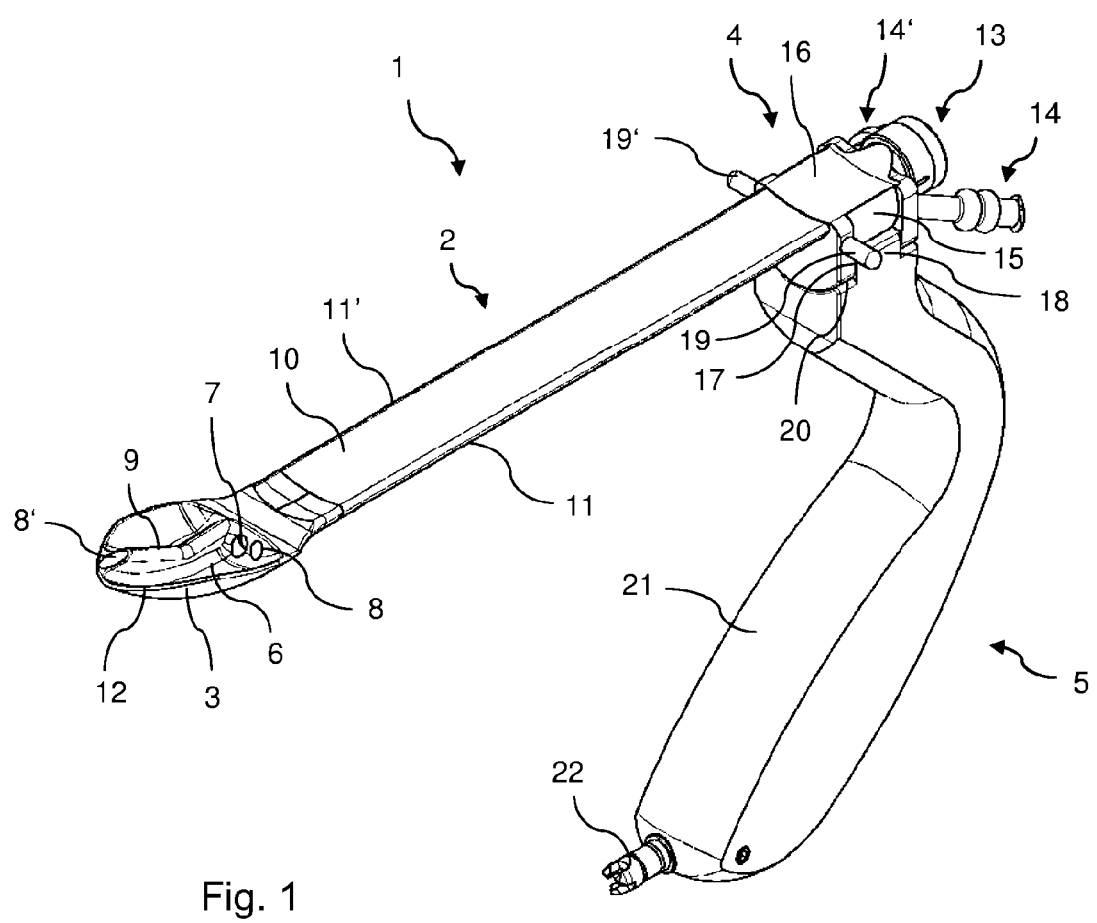
FIG. 1 shows a perspective view of a medical instrument according to a first illustrative embodiment of the invention.

The medical instrument 1 shown in a perspective view in FIG. 1 comprises an elongate shaft 2 which, at its distal end, has a spoon-shaped spatula 3, and, at its proximal end, has a shaft head 4 on which a handle 5 is mounted. The spatula 3 is oriented more or less in a continuation of the shaft 2 but is slightly angled in the direction away from the handle 5, i.e. upward in the view shown in FIG. 1. In its interior, the spoon-shaped spatula 3 forms a hollow space 6. An optics channel 7 and a first rinsing/suctioning channel 8 open into the hollow space 6. A further rinsing/suctioning channel 8' is routed via an angled tube 9 through the hollow space 6 and opens out in the distal end area of the spatula 3. The shaft 2 has a shallow kidney-shaped cross section and has a shallow trough-shaped top face 10. The edges 11, 11' of the shaft 2 and the edge 12 of the spatula 3 are rounded to avoid causing trauma.

An endoscope lens system, which is not shown in FIG. 1, can be introduced into the optics channel 7. It can have an axially directed or angled eyepiece or also, for example, an electronic imager for recording and forwarding an endoscopic image to an evaluation and display device. The endoscope lens system is preferably designed as an oblique optic with a viewing direction at an angle of 30° or 45° to the longitudinal axis, which permits observation of the hollow space 6 formed by the spatula 3 and also of a hollow space held free by the spatula in the tissue or also of a natural hollow space. A surgical manipulation, for example the dissection and separation of tissue, can be performed in the hollow space via working instruments that are inserted parallel to the shaft 2.

In its proximal end area, the shaft 2 is connected rigidly to the shaft head 4, which carries a coupling 13 and also two rinsing/suctioning attachments 14, 14'. The coupling 13 permits the fixing of a rigid endoscope lens system pushed in through the optics channel 7 into the instrument 1. The coupling 13 is arranged at the proximal end of the optics channel 7 routed through the shaft 2 and the shaft head 4. The rinsing/suctioning attachments 14, 14' are connected to the rinsing/suctioning channels 8, 8' and can, for example, be designed in the conventional manner as Luer locks. The optics head further comprises a body 15 with a top face 16 which has a shallow trough-shaped design and substantially forms a continuation of the top face 10 of the shaft 2 in the proximal direction. On the outer face of the instrument 1 lying opposite the handle 5, namely the top face in the view shown in FIG. 1, this results in a substantially smooth surface, free of projections or steps, which extends continuously from the proximal end area of the instrument 1 to the distal end of the shaft 2 and opens at the distal end into the hollow space 6 of the spoon-shaped spatula 3.

On its underside directed away from the top face 16, the body 15 of the shaft head 4 has an arc-shaped groove 17 into which, with a complementary shape, a projection 18 of the handle 5 is inserted. As is explained in more detail below, the handle is held with a form fit in the groove 17 and, by movement of the projection 18 along the arc-shaped groove 17, is pivotable about a rotation axis parallel to the longitudinal axis of the shaft 2. To limit the pivoting angle, the body 15 carries two abutment pins 19, 19' against which a respective corresponding shoulder 20 of the handle 5 abuts when an end angle is reached. The handle 5 is approximately S-shaped overall and, in its lower part, has a grip surface 21, which can be provided with grip dimples (not shown in FIG. 1). At the lower end, the handle 5 carries a retaining pin 22, with which the handle 5 and thus the instrument 1 can be connected to a conventional instrument holder system.

Figure 2:
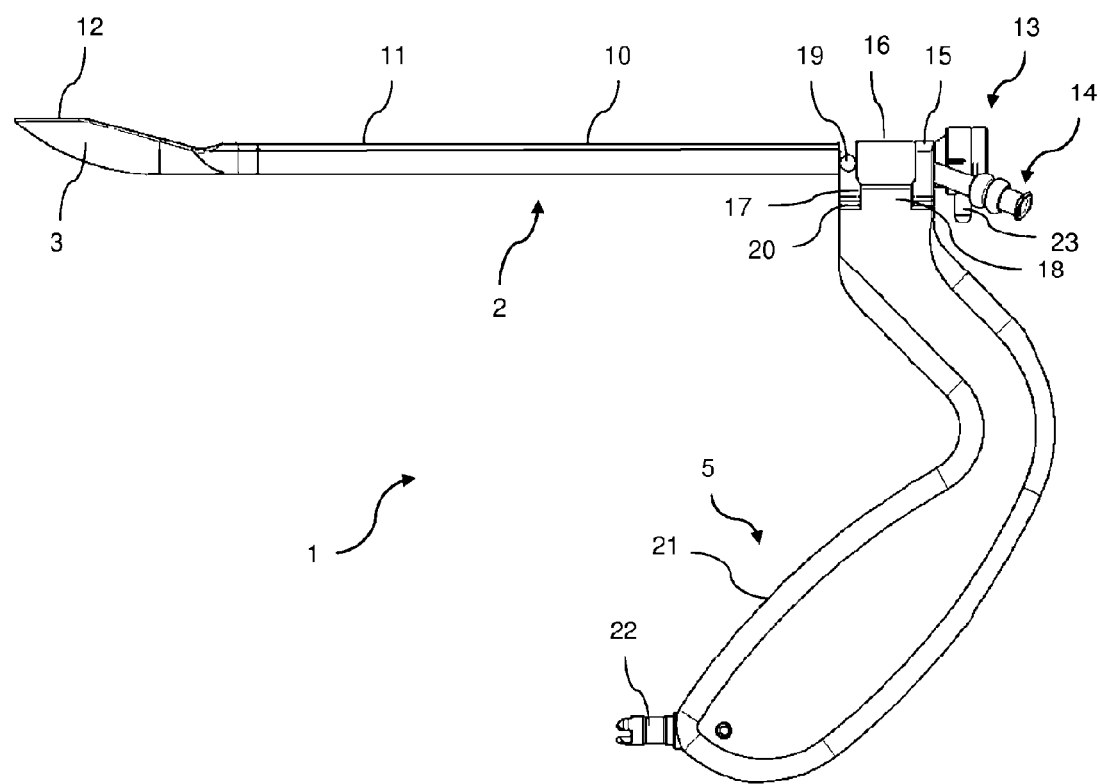
FIG. 2 shows the medical instrument from FIG. 1 in a side view.

It will be seen from the side view in FIG. 2 that the top face 10 of the shaft merges almost seamlessly into the top face 16 of the body 15 of the shaft head 4. The spatula 3 is angled slightly upward in relation to the shaft 2. FIG. 2 also shows a locking pin 23 which, when actuated, allows an endoscope lens system inserted into the instrument 1 to be locked and unlocked again with the aid of the coupling 13.

Figure 3:
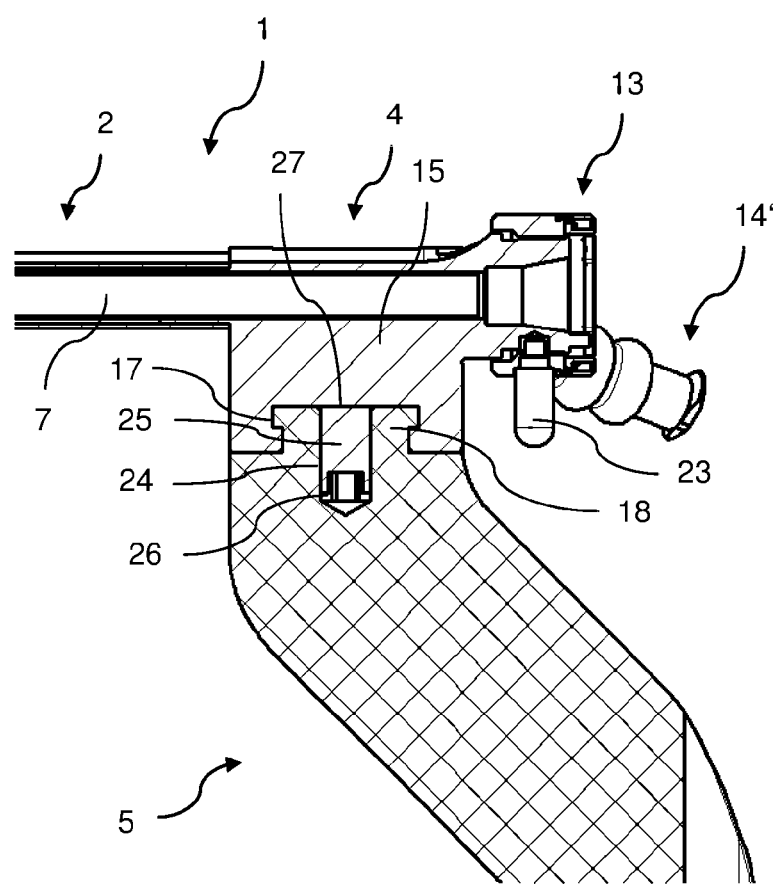
FIG. 3 shows an enlarged partial cross section of the instrument from FIG. 1.

As is shown in an enlarged longitudinal cross section in FIG. 3, the groove 17 is configured with an undercut into which the complementary T-shaped projection 18 of the handle 5 engages. Inside the handle 5, a brake pin 25 is mounted displaceably in a bore 24, and it is pressed by a spring 26 against a friction surface 27 on the base of the T-shaped groove 17 of the body 15 of the shaft head 4. Only one rinsing/suctioning attachment 14' is shown in FIG. 3.

FIG. 3 also shows the optics channel 7 running continuously through the shaft 2 and the shaft head 4 and terminating at the proximal end in the coupling 13.

Figure 4:
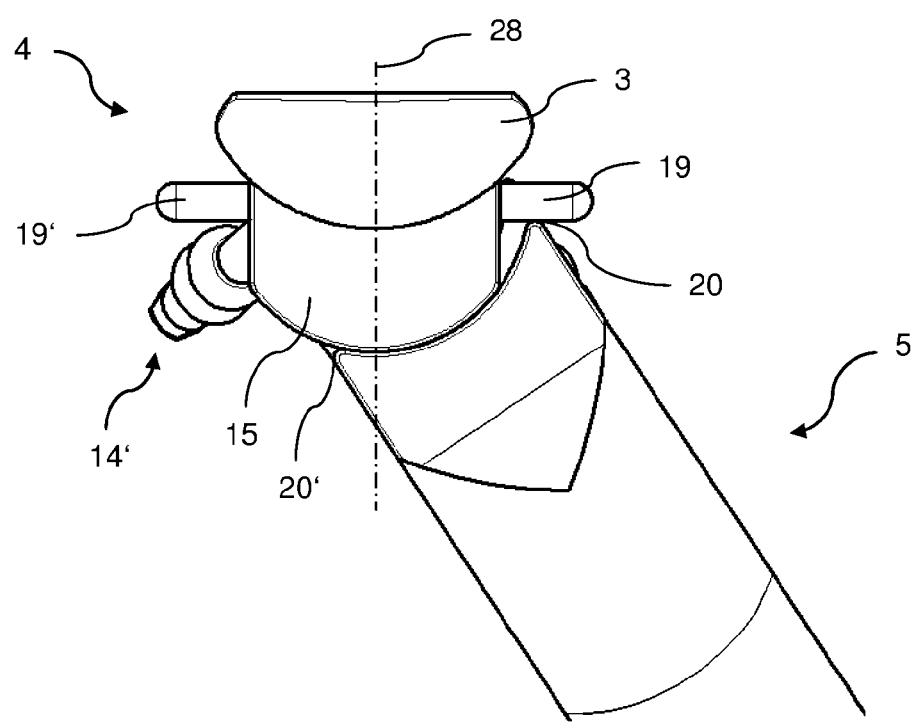
FIG. 4 shows the instrument from FIG. 1 in an enlarged front view, with the handle pivoted out from the central position.

FIG. 4 shows a partial view of the instrument 1, as seen from the distal direction, with the spatula 3 and the body 15 of the optics head 4. The shaft 2 is concealed by the spatula 3. FIG. 4 shows the handle 5 in an angled position; this is an end angle position in which a shoulder 20 is in abutment against an abutment pin 19. In the central position, the central plane of the handle 5 coincides with the longitudinal central plane 28 of the instrument; at the maximum excursion in the other direction (not shown in FIG. 4), the other shoulder 20' abuts against the other abutment pin 19'. The possible rotation movement of the handle 5 is thus limited for example to an angle range, arranged symmetrically with respect to the central position, of approximately ±35°. The rotation axis, which is defined by the center point of the arc-shaped groove 17, coincides for example with the longitudinal central axis of the optics channel 7 (see FIG. 1). The T-shaped groove 17 can, at its base, extend about an angle range of ca. 150° (see also FIG. 5).

Figure 5:
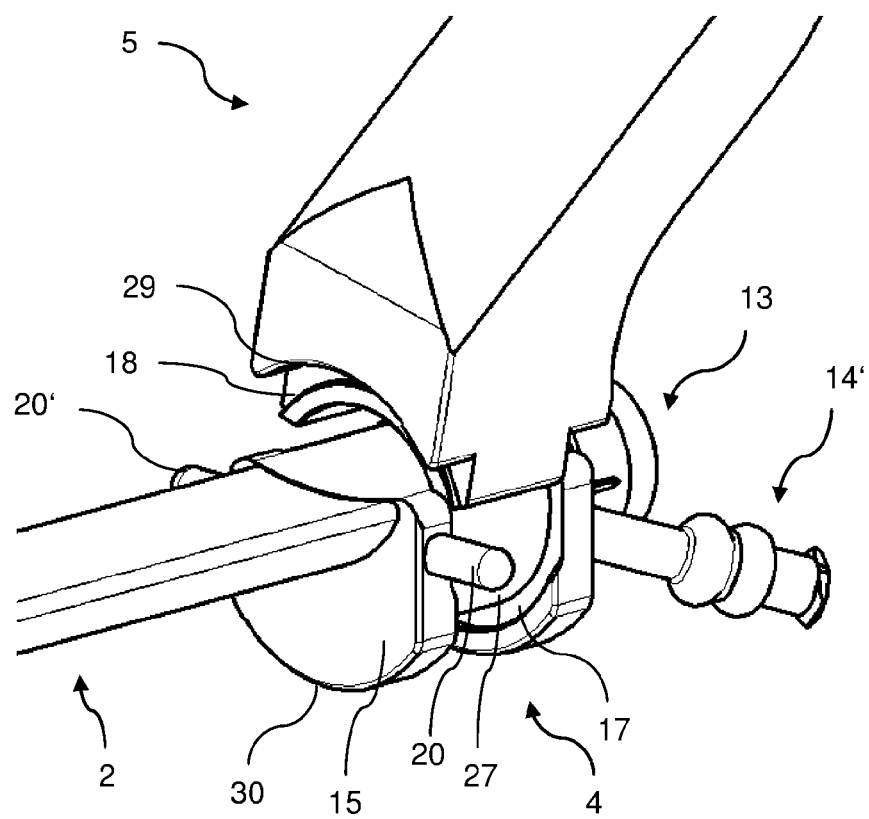
FIG. 5 shows, in a perspective partial view, an intermediate step in the assembly of the handle of the embodiment shown in FIG. 1.

As is shown in FIG. 5, the handle 5 can be connected to the shaft head 4 by means of the handle 5 being inserted with its T-shaped projection 18, which is arc-shaped like the groove 17, into the T-shaped groove 17. An adjoining outer contour 29 of the handle 5 is also arc-shaped and bears on a corresponding outer contour 30 of the body 15 of the shaft head 4. When attaching the handle 5, the brake pin 25 (see FIG. 3) is pressed into the bore 24 using a finger or an auxiliary tool, until the projection 18 of the handle 5 is inserted so far into the groove 17 that the brake pin 25 is held in the bore 24 by contact with the friction surface 27. To connect the handle 5 to the shaft head 4, one of the abutment pins 19, 19' is released from the body 15 of the shaft head 4, and it is reattached after the projection 18 has been inserted into the groove 17 and the handle 5 has almost reached its central position (not shown in FIG. 5). The abutment pins 19, 19' can be designed to be screwable into the body 15 of the shaft head 4 and to be removable therefrom again, in order to create a releasable connection of the handle 5 to the shaft head 4. However, if the connection between the handle 5 and the shaft head 4 is not intended to be able to be released by a user, the abutment pins 19, 19' are rigidly connected to the shaft head 4, for example by adhesive bonding of the screw thread.

Figure 6:
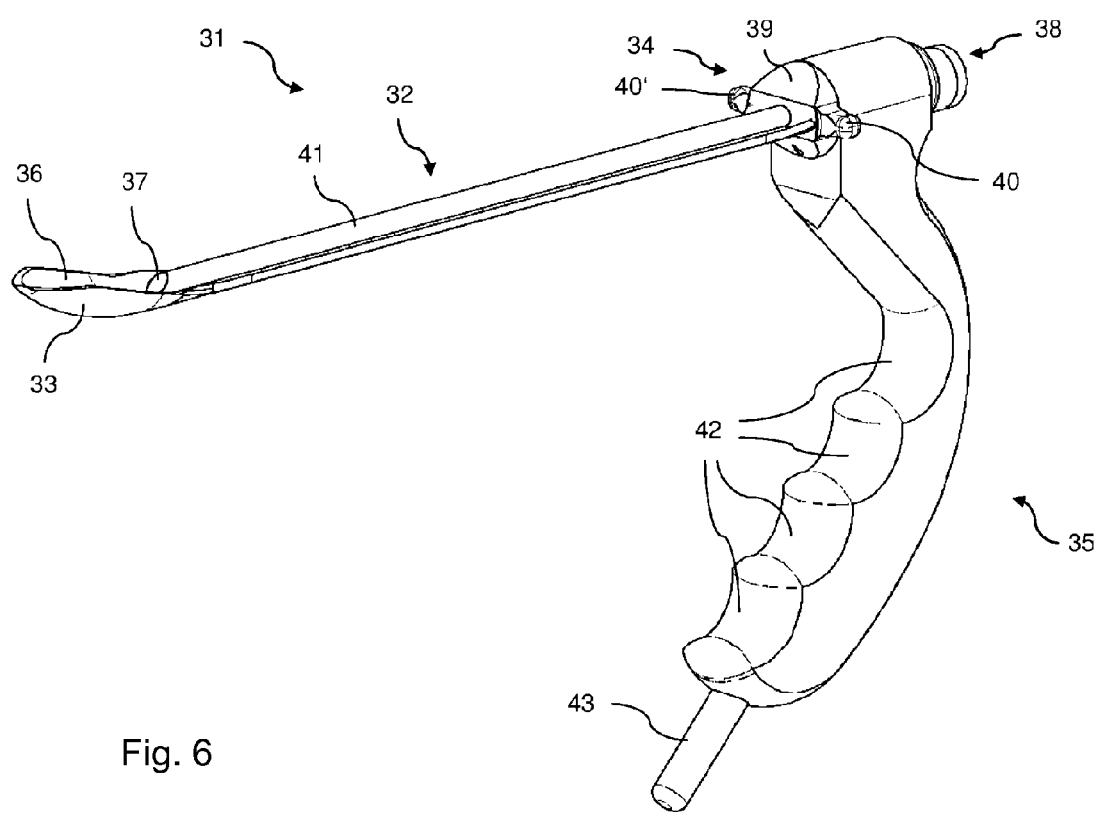
FIG. 6 shows a perspective view of a medical instrument according to a second illustrative embodiment of the invention.

According to the second illustrative embodiment of the invention shown in FIG. 6, a medical instrument 31 has an elongate shaft 32, a spoon-shaped spatula 33 arranged at the distal end of the shaft 32, a shaft head 34 at the proximal end of the shaft 32, and a laterally protruding handle 35 attached to the shaft head 34. The shaft 32 is trough-shaped, wherein a tube 41 with a continuous optics channel 37 is arranged inside the groove, which optics channel 37 ends in an opening leading into the hollow space 36 formed by the spoon-shaped spatula 33. At the proximal end of the shaft, the optics channel 37 continues through the shaft head 34 and ends in a coupling 38, with the aid of which an endoscope lens system pushed into the optics channel 37 can be fixed on the medical instrument 31. The shaft head 34 comprises a front wall 39 which is stationary relative to the shaft 32 and which carries two laterally protruding holding pins 40, 40' connected rigidly to the front wall 39. In the proximal direction from the front wall 39, the handle engages around a portion of the shaft head 34 designed as a rotary bearing. The handle 35 is curved approximately in an S shape and, in the lower area arranged at an angle with respect to the distal end of the instrument 31, has a plurality of grip dimples 42, which make it easier for the user to obtain an ergonomic and secure hold of the handle 35 with one hand. At the lower end, the handle 35 carries a retaining pin 43, with which the handle 35 and therefore the medical instrument 31 can be inserted into a conventional holding system and be held there. The handle 35 is rotatable about the central longitudinal axis of the optics channel 37 relative to the shaft 32 and relative to the shaft head 34, which is rigidly connected to the shaft 32. To effect the rotation, a user can hold the shaft head 34 at the holding pins 40, 40' and turn the handle 35 against the shaft head 34. The angle of rotation can be limited by an abutment (not shown). Otherwise, the medical instrument 31 is designed in the same way as in the first illustrative embodiment and can, in particular, have one or more rinsing/suctioning channels (not shown) with corresponding attachments.

Before the medical instrument 1, 31 shown in the figures is used, an endoscope lens system is inserted from the direction of the proximal end through the optics channel 7, 37 until it reaches the distal opening of the optics channel 7, 37, or reaches slightly beyond this, such that endoscopic viewing at least of the hollow space 6, 36 formed by the spatula 3, 33 is possible. The inserted endoscope lens system is locked with the coupling 13, 38 and is connected, for example, to a light-carrying cable through which illumination light generated by an external light source is introduced. If appropriate, suctioning/rinsing lines can be attached to the suctioning/rinsing attachments 14, 14' at this time or at a later time.

To reach the operating site when performing thyroid surgery using the EndoCATS technique, the handle 5, 35 of the medical instrument 1, 31 is gripped by the user, and the spatula 3, 33 is inserted with the shaft 2, 32 through an incision made behind the ear of the patient. With endoscopic monitoring, which is done through an eyepiece of the endoscope lens system or also by displaying the endoscopic image on a screen, the spatula 3, 33 is guided through natural spaces. If a rotation of the spatula 3, 33 and of the shaft 2, 32 about the longitudinal axis is needed depending on the orientation of the spaces in question, this can be done by suitable rotation of the handle 5, 35. In order to extend the possible range of angles of rotation or also to permit improved handling, it is instead or additionally possible to use a rotation movement between the shaft head 4, 34 and the handle 5, 35. For this purpose, the user grips the abutment pins 19, 19' or the holding pins 40, 40' and turns the shaft head 4, 34 and thus the shaft 2, 32 with the spatula 3, 33 about a rotation axis parallel to the longitudinal axis of the shaft 2, 32 relative to the handle 5, 35, wherein the friction resistance generated by the brake pin 25 which presses on the friction surface 27 has to be overcome. The rotation axis, which is defined by the arc-shaped groove 17 for example, can be arranged such that it substantially corresponds to the longitudinal axis of an endoscope lens system inserted into the optics channel 7, 37. In this way, endoscopic viewing is made easier during the insertion and rotation of the shaft 2, 32.

When the spatula 3, 33 has been advanced as far as the actual operating site, for example the thyroid bed (spatium de Quervain), endoscopic working instruments are advanced parallel to the shaft 2, 32 into the operating site. In the above-described first illustrative embodiment of the invention, this is facilitated by the fact that the top faces 10, 16 of the shaft 2 and of the body 15 of the shaft head 4 form a substantially continuous plane surface or a shallow trough, on or in which the endoscopic working instruments can be advanced. With the working instruments, surgical manipulations can be carried out with endoscopic monitoring in the hollow space 6, 36 formed by the spatula 3, 33 or in a hollow space that is further widened and held open by the spatula 3, 33 pressing on the surrounding tissue. For example, a lobe of the thyroid can be exposed and, by withdrawing the shaft 2, 32 with the spatula 3, 33, can be held in the hollow space 6, 36 of the spatula 3, 33 and thus be completely concealed. This too can be made easier by the design of the top faces 10, 16 of the shaft 2 and of the body 15 of the shaft head 4 as a substantially continuous flat surface or shallow trough, in accordance with the first illustrative embodiment of the invention.

The operating site can be irrigated by way of the rinsing/suctioning channels 8, 8', wherein the rinsing/suctioning channel 8' opening out near the optics channel 7 also permits rinsing of the window of the inserted endoscope lens system. The rinsing liquid and, if appropriate, bodily fluids and/or smoke gases, which may develop during use of electrosurgical working instruments, can likewise be suctioned through the rinsing/suctioning channels 8, 8'.

For the sake of clarity, not all reference signs are shown in all of the figures. Reference signs that are not explained in connection with one figure have the same meaning as in the other figures.

What is claimed is:

1. A medical instrument, comprising:
    an elongate shaft which, at a distal end, carries a spatula, and, in a proximal end area, has a shaft head on which a laterally protruding handle is arranged, wherein the shaft is rotatable relative to the handle about a rotation axis parallel to a longitudinal axis of the shaft;
    wherein the handle is guided relative to the shaft head in an arc-shaped-groove that extends transversely with respect to the longitudinal axis of the shaft;
    wherein at least one abutment pin is arranged to limit an angle range of the rotation between the handle and the shaft head;
    wherein the handle is connected releasably to the shaft head;
    after removal of the at least one abutment pin, the handle in the groove can be moved beyond the range limited by the abutment pin and in this way can be separated from the head of the shaft, wherein the groove has a T-shaped or a dovetail-shaped.

2. The medical instrument according to claim 1, wherein the shaft is rotatable against a frictional resistance.

3. The medical instrument according to claim 2, wherein, in order to generate the frictional resistance, a spring-mounted brake pin or a spring-mounted pressure piece is provided.

4. The medical instrument according to claim 3, wherein the brake pin or the pressure piece is assigned to the handle and acts on a friction surface of the shaft head.

5. The medical instrument according to claim 1, wherein the shaft is flattened out on a top face and, together with a top face of the shaft head, forms a substantially continuous surface.

6. The medical instrument according to claim 1, wherein the groove is arranged in a body of the shaft head, and in that the handle has at least one projection with a shape matching the groove and engaging with a form fit in the groove.

7. The medical instrument according to claim 2, wherein the shaft is flattened out on a top face and, together with a top face of the shaft head, forms a substantially continuous surface.

8. The medical instrument according to claim 5, wherein the substantially continuous surface is a substantially continuous flat surface.

9. The medical instrument according to claim 5, wherein the substantially continuous surface is a substantially continuous shallow trough surface.

10. A medical instrument, comprising:
an elongate shaft extending along a longitudinal axis between a distal end area and a proximal end area, the shaft having a shaft head at the proximal end area;
a spatula carried at the distal end of the shaft;
a handle releasably connected to and laterally protruding from the shaft head, the handle being guided relative to the shaft head in an arc-shaped groove that extends transversely with respect to the longitudinal axis of the shaft such that the shaft is rotatable relative to the handle about a rotation axis parallel to the longitudinal axis of the shaft;
an abutment pin releasably connected to the shaft head and arranged to limit an angle range of the rotation between the handle and the shaft head, the abutment pin being configured such that, after the abutment pin is unconnected from the shaft head, the handle can be moved beyond the range limited by the abutment pin so as to permit the handle to be unconnected from the shaft head, wherein the groove has a T-shaped or a dovetail-shaped.

11. The medical instrument according to claim 1, wherein the groove extends transversely with respect to the longitudinal axis of the shaft along an entirety of a length of the groove.

12. The medical instrument according to claim 10, wherein the groove extends transversely with respect to the longitudinal axis of the shaft along an entirety of a length of the groove.

* * * * *